(12) United States Patent
Devine

(10) Patent No.: US 10,369,041 B2
(45) Date of Patent: Aug. 6, 2019

(54) EYE MASK FOR AMELIORATION OR PREVENTION OF DRY EYE AND THE LIKE

(71) Applicant: John Devine, Tempe, AZ (US)

(72) Inventor: John Devine, Tempe, AZ (US)

(73) Assignee: John Devine, Tempe, AZ (US)

( * ) Notice: Subject to any disclaimer, the term of this patent is extended or adjusted under 35 U.S.C. 154(b) by 1003 days.

(21) Appl. No.: 14/311,573

(22) Filed: Jun. 23, 2014

(65) Prior Publication Data

US 2015/0012074 A1 Jan. 8, 2015

Related U.S. Application Data

(63) Continuation-in-part of application No. 13/936,301, filed on Jul. 8, 2013, now abandoned.

(51) Int. Cl.
| | |
|---|---|
| *A61F 7/08* | (2006.01) |
| *A61F 7/00* | (2006.01) |
| *A61F 7/02* | (2006.01) |
| *A61F 9/04* | (2006.01) |

(52) U.S. Cl.
CPC ............... *A61F 7/007* (2013.01); *A61F 7/02* (2013.01); *A61F 9/04* (2013.01); *A61F 2007/0004* (2013.01); *A61F 2007/0071* (2013.01); *A61F 2007/0077* (2013.01); *A61F 2007/0223* (2013.01); *A61F 2007/0228* (2013.01)

(58) Field of Classification Search
CPC ..... A61F 7/007; A61F 7/02; A61F 2007/0004
See application file for complete search history.

(56) References Cited

U.S. PATENT DOCUMENTS

| | | | | |
|---|---|---|---|---|
| 2,038,275 A | * | 4/1936 | Fogg | H05B 3/342 165/46 |
| 3,173,419 A | * | 3/1965 | Dubilier | A61F 7/007 165/136 |
| 4,261,364 A | | 4/1981 | Haddad et al. | |

(Continued)

FOREIGN PATENT DOCUMENTS

| | | | |
|---|---|---|---|
| CN | 102349763 A | * | 2/2012 |
| DE | 29914199 | | 8/1999 |

(Continued)

OTHER PUBLICATIONS

International Search Report and Written Opinion of International Application No. PCT/US2014/045187, dated Oct. 7, 2014, 14 pages.

(Continued)

*Primary Examiner* — Kaitlyn E Smith
*Assistant Examiner* — Yasamin Ekrami
(74) *Attorney, Agent, or Firm* — Polansky & Associates, P.L.L.C.; Paul J. Polansky

(57) ABSTRACT

In one form, an eye mask includes an eye mask core assembly, a band, and first and second insulated wires. The eye mask core assembly has first and second heat producing areas separated by a distance corresponding to a separation of human eyes and having first and second ends. The eye mask core assembly produces heat in response to the application of a voltage thereto. The covering surrounds the eye mask core assembly. The band is attached to the first and second ends of said eye mask core assembly. The first and second insulated wires have first ends connected to the eye mask core assembly, and second ends for connection to a power supply.

20 Claims, 4 Drawing Sheets

(56) References Cited

U.S. PATENT DOCUMENTS

| | | | | |
|---|---|---|---|---|
| 4,279,039 | A | * | 7/1981 | Drew ................. A42B 1/12 2/428 |
| 5,126,533 | A | * | 6/1992 | Newman ........... H01L 21/67103 219/200 |
| 5,700,238 | A | * | 12/1997 | Hyson ................. A61F 9/04 128/858 |
| 5,802,620 | A | * | 9/1998 | Chiang ............... A63B 33/002 2/428 |
| 6,155,995 | A | | 12/2000 | Lin |
| 6,263,158 | B1 | * | 7/2001 | Rutherford ............. H05B 3/36 219/544 |
| 6,283,931 | B1 | * | 9/2001 | Augustine ............... A61F 7/007 602/14 |
| 7,584,754 | B1 | * | 9/2009 | Pellegrini ................ A61F 9/04 128/858 |
| 7,976,573 | B2 | | 7/2011 | Korb et al. |
| 2005/0137649 | A1 | * | 6/2005 | Paul, Jr. ................ A61N 1/326 607/53 |
| 2007/0060988 | A1 | * | 3/2007 | Grenon .................... A61F 9/00 607/96 |
| 2008/0132978 | A1 | | 6/2008 | Korb et al. |
| 2012/0222192 | A1 | | 9/2012 | Carey et al. |
| 2013/0172829 | A1 | * | 7/2013 | Badawi ................ A61F 9/0008 604/294 |
| 2013/0184782 | A1 | * | 7/2013 | Eipper ............... A61N 1/36046 607/53 |

FOREIGN PATENT DOCUMENTS

| | | | |
|---|---|---|---|
| JP | WO98/10723 | 3/1998 | |
| JP | WO 9810723 A1 * | 3/1998 | ............ A61F 7/007 |
| JP | H1085248 | 4/1998 | |
| JP | 2006-198249 | 8/2006 | |

OTHER PUBLICATIONS

Kevin Holzmeister, Recommendation Letter Regarding Blepharitis Treatment Mask, Aug. 23, 2013, 1 page.

P. Strøm-Tejsen, D.P. Wyon, L. Lagercrantz and L. Fang, "Occupant Evaluation of 7-Hour Exposures in a Simulated Aircraft Cabin—Part 1: Optimum Balance Between Fresh Air Supply and Humidity," Proceedings: Indoor Air 2005, pp. 40-45.

SAE International; "Standard for 12 Volt Cigarette Lighters, Power Outlets, and Accessory Plugs"; ANSI J563; 1960-2009; 1 page.

* cited by examiner

EYE MASK FOR AMELIORATION OR PREVENTION OF DRY EYE AND THE LIKE

This application is a continuation-in-part of application Ser. No. 13/936,301, filed Jul. 8, 2013, entitled "Eye Mask for Amelioration or Prevention of Dry Eye and the Like," invented by the inventor hereof.

FIELD

This disclosure relates generally to health devices, and more specifically to devices for the treatment of human eyes.

BACKGROUND

In the human eye, the tear film covering the ocular surfaces is composed of three layers. The innermost layer in contact with the ocular surface is the mucus layer. The mucus layer is comprised of many mucins. The middle layer comprising the bulk of the tear film is the aqueous layer. The aqueous layer is important in that it provides a protective layer and lubrication to prevent dryness of the eye. Dryness of the eye can cause symptoms such as itchiness, burning, and irritation, which can result in discomfort. The outermost layer is comprised of many lipids known as "meibum" or "sebum." This outermost lipid layer is very thin, typically less than 250 nm in thickness. The lipid layer provides a protective coating over the aqueous and mucus layers to limit the rate at which these underlying layers evaporate. A higher rate of evaporation of the aqueous layer can cause dryness of the eye. Thus, if the lipid layer is not sufficient to limit the rate of evaporation of the aqueous layer, dryness of the eye may result. The lipid layer also lubricates the eyelid during blinking, which prevents dry eye. If the lipid layer can be improved, the rate of evaporation is decreased, lubrication is improved, and partial or complete relief of the dry eye state is achieved.

One environment which can contribute to dry eye is an airplane cabin. The interior of a pressurized airplane cabin has very low relative humidity, such as between 10 and 20%. Long airplane flights can severely irritate the eyes and cause dry eye.

Dry eye can also be caused by a condition known as meibomian gland dysfunction (MGD). Known treatments for MGD generally apply significant heat in order to melt, loosen, or soften of obstructions or occlusions in the meibomian glands. Regarding electrical heaters, one known eye treatment is described in U.S. Patent Pub. No. 2007/0060988. The heater it describes applies heat by using an electrical signal requiring the use of a thermocouple and sophisticated feedback control system to monitor and adjust the electrical signal to maintain heat between 43 and 47 degrees C. to one eye for between 1 and 10 minutes. Furthermore, the device uses a screw to adjust pressure on the eye. Because it requires 1) a threaded shaft or screw adjustment, 2) elevated heat, and 3) precise thermal regulation independent of temperature, the time of treatment, actual temperature, and pressure on the eye must be administered and monitored by a medical physician or technician to avoid burning the eyelid or damaging the eye itself. Another heater is described in U.S. Pat. No. 4,261,364. The heater it describes uses a battery operated surgical heater that warms a compress resembling an eye patch for post-ophthalmic surgery patients. The heater is strapped to a surgical compress that applies heat to a patient's eye socket. Since the heater 1) is in molded plastic not integrated with the compress, 2) is battery operated, 3) uses wiring for a heating element, and 4) heats a compress rather than an eyelid, the result is an uncomfortable, uncontrolled heat source that cannot carefully control the temperature that reaches the eyelid itself. Because of these factors, the time of treatment, actual temperature, and pressure on the eye must also be administered and monitored by a medical physician or technician to avoid burning the eyelid or damaging the eye itself.

Figure 1:
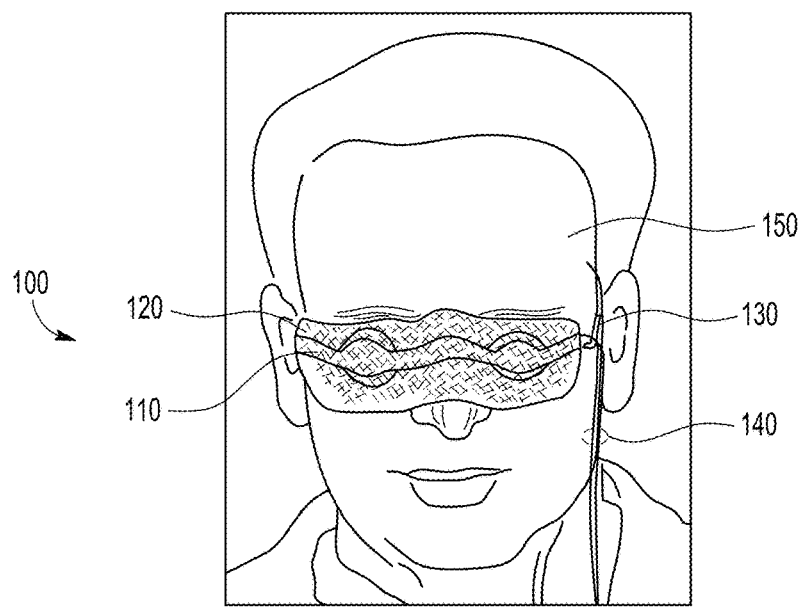
FIG. 1 illustrates a front view of an eye mask worn by a human according to some embodiments.

In the following description, the use of the same reference numerals in different drawings indicates similar or identical items. Moreover unless otherwise noted, the word "coupled" and its associated verb forms include both direct connection and indirect electrical connection by means known in the art, and unless otherwise noted any description of direct connection implies alternate embodiments using suitable forms of indirect electrical connection as well.

DETAILED DESCRIPTION OF ILLUSTRATIVE EMBODIMENTS

FIG. 1 illustrates a front view of an eye mask 100 worn by a human 150 according to some embodiments. Eye mask 100 includes an eye mask core assembly 110 surrounded by a covering 120 and attached just above the ears using a band 130 made of a suitable flexible material such as an elastomer (commonly referred to as an elastic). Eye mask 100 has a set of two insulated wires 140 attached to eye mask core assembly 110 on the left side (from the wearer's perspective) for connection to a suitable source of power as will be explained further below.

In general, eye mask 100 is intended to ameliorate dry eye and thus applies a lower amount of heating than known MGD eye treatment devices. In the illustrated embodiment, eye mask 100 increases the temperature of the surface of the eyelids by about 3 degrees Celsius (° C.) to about 40° C., instead of 43-47° C., and always keeps them below 42° C. This lower temperature allows the wearer to wear eye mask 100 for an extended and possibly indefinite period of time without eye damage or discomfort. Thus it is appropriate for use by an air traveler who may fall asleep and fail to remove it after 10 minutes. As will be explained below, eye mask 100 uses a resistive heating system that produces a relatively constant temperature and only requires the application of a relatively stable DC voltage, without the need for thermal feedback. Thus, eye mask 100 can be used with various power supplies and can be made cheaply.

Covering 120 effectively spreads and holds the heat generated by eye mask core assembly 110 across the whole surface of the eyes, allowing low power dissipation. In one embodiment, covering 120 is formed by cotton cloth. When powered by a DC power supply of 5.0 volts, covering 120 is preferably formed with a cotton cloth about 0.25 mm thick. When powered by a DC power supply of 6.0 volts, covering 120 is preferably formed with a cotton cloth about 0.51 mm thick. Eye mask 100 is a hands-free mask that applies heat to both eyes and does not require a medical physician or technician for administration. Moreover it is adjustable for different wearers as will be described further below.

Figure 2:
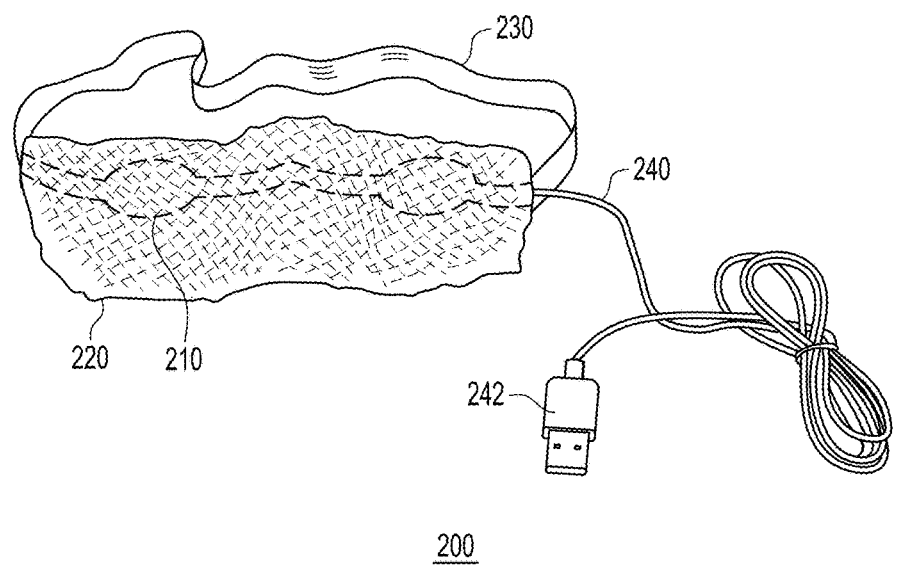
FIG. 2 illustrates a front view of an eye mask adapted for receiving power from a universal serial bus (USB) port according to one embodiment.

FIG. 2 illustrates a front view of an eye mask 200 adapted for receiving power from a universal serial bus (USB) port according to one embodiment. Eye mask 200 includes an eye mask core assembly 210 surrounded by a covering 220 and connected to a band 230 made of a suitable material such as elastic. Thus eye mask 200 can fit a variety of different head sizes, interpalprebal distances, and nasal bridge heights. Eye mask 200 has a cable 240 having two insulated wires. Cable 240 has a first end attached to eye mask core assembly 210 on the left side (from the wearer's perspective) and a second end electrically and mechanically attached to a USB connector 242. In this embodiment, eye mask 200 is capable of connecting to and receiving power from a USB host such as a laptop computer. Thus the user can power eye mask 200 using the laptop computer's battery. Typical laptop computer batteries are formed with lithium ion or lithium polymer technology which provides sufficient capacity to power the eye mask for an extended period of time. In addition some commercial airline flights provide a seat power jack which allows the laptop computer to be powered from the airplane's power supply, which avoids depleting the battery charge.

In another embodiment, connector 242 could be a connector substantially compliant with the American National Standards Institute/Society of Automotive Engineers ANSI/SAE J563 standard. This type of connector allows use by, for example, passengers in most automobiles and air travelers with seat power adaptors now available on many commercial airplanes.

Figure 3:
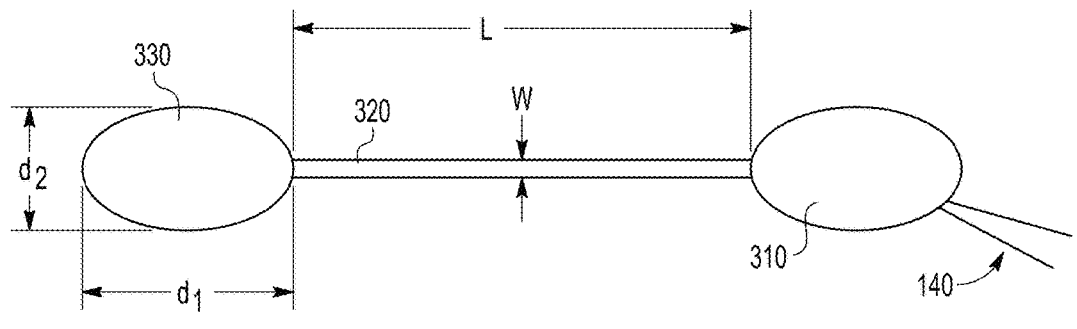
FIG. 3 illustrates a front view of a heating element suitable for use in the eye masks of FIGS. 1 and 2.

FIG. 3 illustrates a front view of a heating element 300 suitable for use in the eye masks of FIGS. 1 and 2. Heating element 300 includes two eye-shaped portions 310 and 330 separated by a center portion 320. Eye-shaped portion 310 is connected to wires 140 and has an internal conductor arranged in a pattern that is designed to produce heat, as will be explained further below. Eye-shaped portion 330 has a similar internal conductor pattern as eye-shaped portion 310. Center portion 320 has a conductor that is not designed to produce heat and electrically connects eye shaped portions 310 and 330.

In one embodiment, heating element 300 is sized for a typical adult. Each eye shaped portion has a longer diameter labeled "d1" of about 25.0 mm, and a shorter diameter labeled "d2" of about 14.0 mm. Center portion 320 has a length labeled "L" of about 66-67 mm, and a width labeled W of about 3-4 mm.

Figure 4:
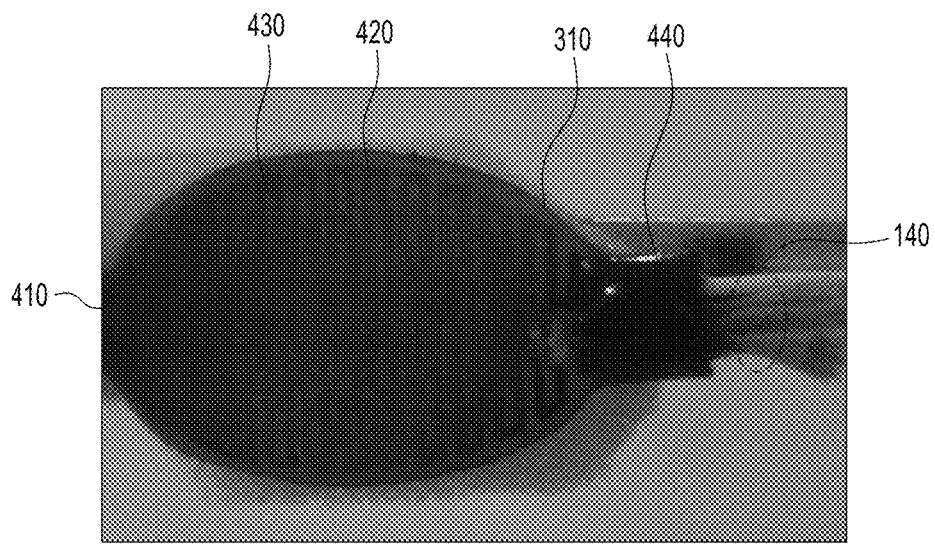
FIG. 4 illustrates a front view of a portion of the heating element of FIG. 3.

FIG. 4 illustrates a front view of a portion 400 of heating element 300 of FIG. 3. Portion 400 shows eye-shaped portion 310, which includes a first end 410 at the center portion, and a second end 440 for the physical and mechanical attachment of wires 140 to respective ends of a conductor 430. Conductor 430 is arranged in a serpentine pattern to increase the resistance and thus dissipate and distribute heat. The serpentine pattern is surrounded on a flexible substrate 420. Flexible substrate 420 is a thin polyimide film substrate having a thickness of about 0.33 millimeters (mm), which provides long flex life and ability to withstand metal etching processes. In one embodiment, conductor 430 is a trace formed with an alloy of nickel. It may be formed on flexible substrate 420 by any suitable process, such as depositing a blanket layer, applying a mask, and etching the serpentine pattern based on the mask.

Figure 5:
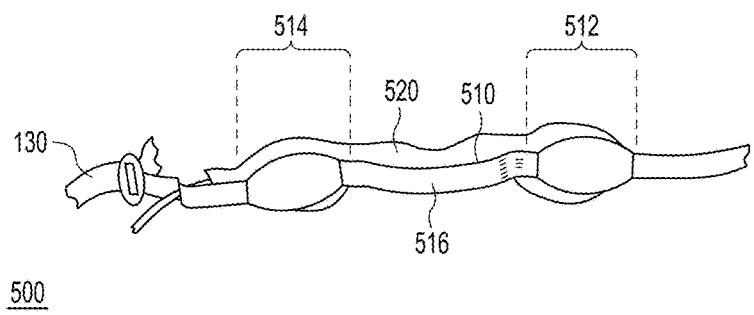
FIG. 5 illustrates a front view of a portion of the eye mask of FIG. 1 including an eye mask core assembly.

FIG. 5 illustrates a front view of a portion of the eye mask of FIG. 1 including an eye mask core assembly 500. Eye mask core assembly 500 includes a support member 510 attached to said first and second ends of band 130. Support member 510 in turn has two eye-shaped portions 512 and 514, respectively, separated by a rectangular center section 516 and surrounded by rectangular ends for attachment to band 130. Center section 516 has a bend in the center to form the eye mask around the bridge of the wearer's nose. Support member 510 is formed of any suitable semi-rigid material to hold the heating element substantially in place over the wearer's eyes. In some embodiments, the semi-rigid material is formed with aluminum having a thickness of about 0.010 mm to about 0.016 mm. Thus it can be adjusted by the user for different head sizes, interpalprebal distances, and nasal bridge heights. Eye mask core assembly 500 also includes a foam insulator 520 on the side of support member 510 closest to the wearer.

Figure 6:
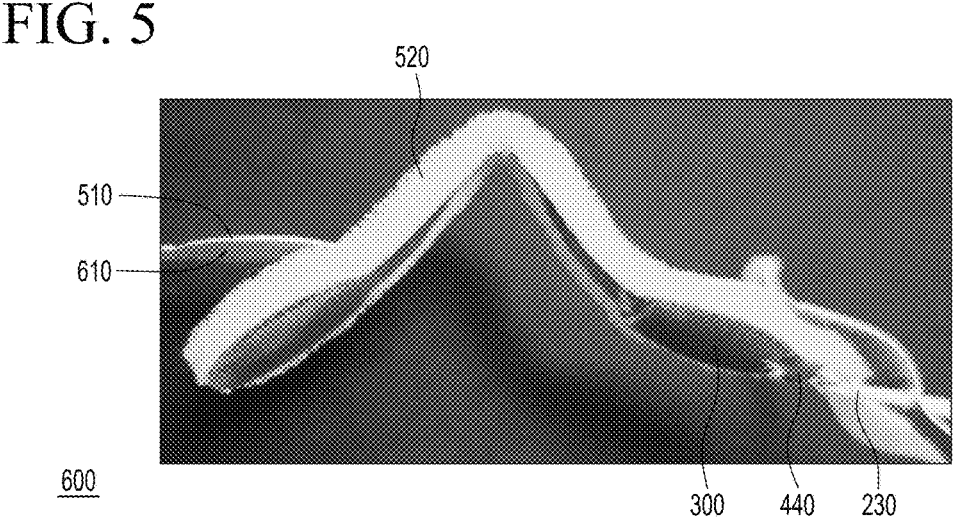
FIG. 6 illustrates a perspective view of an eye mask core assembly.

FIG. 6 illustrates a perspective view 600 of eye mask core assembly 500 of FIG. 5. As shown in FIG. 6, eye mask core assembly 600 includes support member 510 and heating element 300 separated by a foam insulator 520 that applies pressure to gently press heating element 300 against the wearer's eyes. Foam insulator 520 is attached to support member 510 by an adhesive 610 which may be any suitable hypoallergenic adhesive or glue that adheres to support member 510 and foam insulator 520. A similar hypoallergenic adhesive is used to attach heating element 300 to foam insulator 520.

Figure 7:
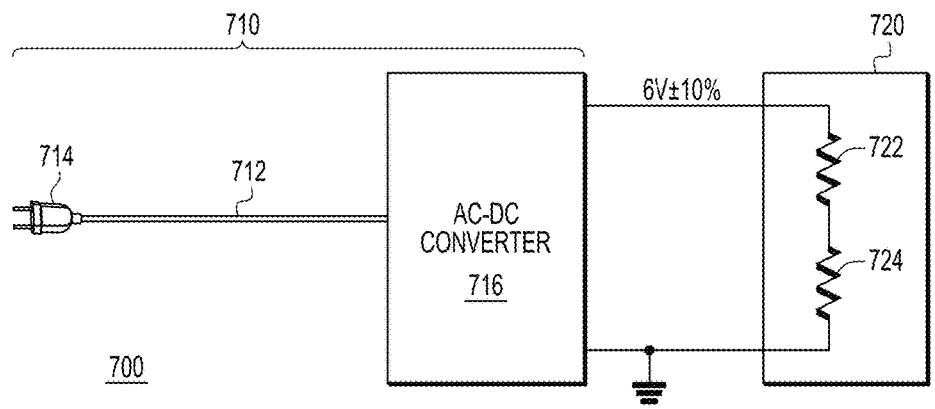
FIG. 7 illustrates in partial block diagram and partial schematic form an electrical diagram of an eye mask according to other embodiments.

FIG. 7 illustrates in partial block diagram and partial schematic form an electrical diagram of an eye mask system 700 according to another embodiment. Eye mask system 700 includes a regulated power supply 710 and a heating element 720 modeled as resistors 722 and 724 representative of the resistance of the serpentine conductor corresponding to the two eye-shaped portions. Eye mask system 700 uses regulated power supply 710 to connect to an alternating current (AC) mains supply and thus eye mask system 700 is suitable for home use. Regulated power supply 710 includes a wire 712 having a first end connected to an AC plug 714, and a second end connected to an AC-DC converter 716. AC-DC converter 716 is a low-cost converter formed with a transformer, an off-line switching regulator, and a small number of discrete components (not shown in FIG. 7) and provides an output voltage of 6 volts±10%.

Eye mask system 700 generates heat using resistive heating elements, and is a feed-forward system that does not require complicated thermal feedback to regulate the temperature at the surface of the wearer's eyes to a precise temperature. Moreover the covering spreads the heat uniformly over the eyes and provides temperature stability. Finally the low power dissipation makes it suitable for use with battery powered devices such as laptop computers for an extended period of time.

Figure 8:
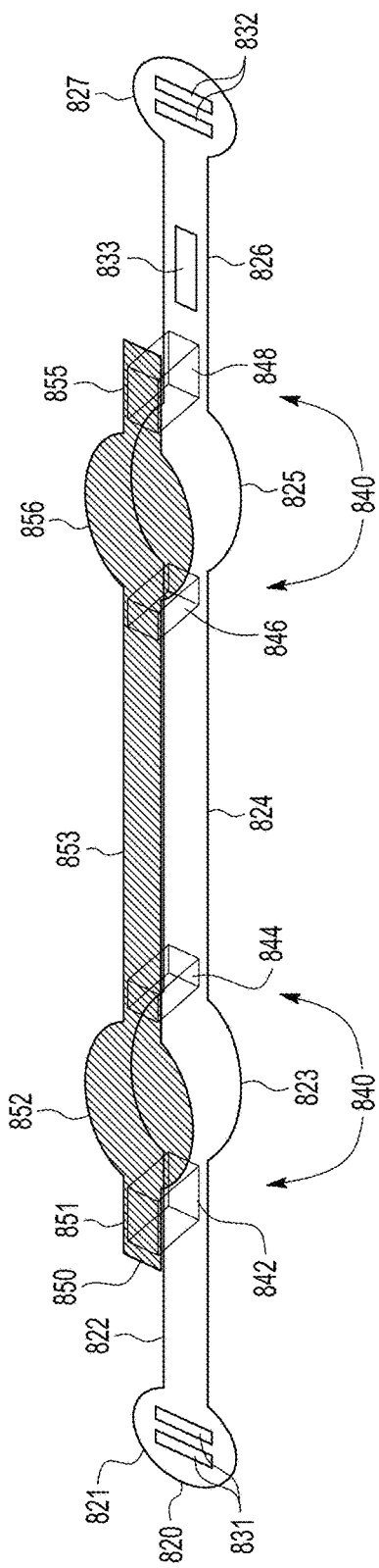
FIG. 8 illustrates a perspective view of an eye mask core assembly according to another embodiment.

FIG. 8 illustrates a perspective view of an eye mask core assembly 800 according to another embodiment. Eye mask core assembly 800 includes generally a support member 820, a set of standoffs 840, and a heating element 850. Support member 820 is underneath heating element 850 and includes generally a first band attachment portion 821, a first side portion 822, a first eye-shaped portion 823, a center nose portion 824, a second eye-shaped portion 825, a second side portion 826, and a second band attachment portion 827. First band attachment portion 821 has two vertical rectangular slits 831 etched or stamped therein, and second band attachment portion 827 likewise has two vertical rectangular slits 832 etched or stamped therein. A first end of the band is inserted in the inside one of vertical rectangular slits 831 and then looped back through the outer one of vertical rectangular slits 831. Likewise a second end of the band is inserted in the inside one of the vertical rectangular slits 832 and then looped back through the outer one of vertical rectangular slits 832. The elasticity of the bands allows the user to secure eye mask core assembly 800 comfortably to his or her head. An opening 833 is provided to connect and route the wires to heating element 850 away from the user's head.

Standoffs 840 include standoffs 842, 844, 846, and 848. Each standoff is made of a soft, flexible material such as foam and is attached to support member 820 at the sides of eye shaped portions 823 and 825 using a suitable adhesive. Likewise, the other ends of standoffs 840 are attached to corresponding portions of heating element 850. In the embodiment shown in FIG. 8, outer standoffs 842 and 848 are wider in width than inner standoffs 844 and 846.

Heating element 850 includes a first end 851, a first eye-shaped portion 852, a center portion 853, a second eye-shaped portion 854, and a second end 855. Eye-shaped portions 852 and 854 have substantially the same size and shape of eye-shaped portions 823 and 825 of support member 820. Second end 855 has exposed contacts for connection to a wire. Heating element 850 can be formed using a serpentine conductor as described above. In this additional embodiment, heating element 850 heats the surface of the eyelid to a temperature of about 40° C.

During construction of eye mask core assembly 800, the center portions 824 and 853 of support member 820 and heating element 850, respectively, are bent to correspond to the shape of a human nose. Moreover, each of ends 851 and 855 of heating element 850 are bent to fit conformally around the outer side of a corresponding one of standoffs 842 and 848. The end of the wire opposite the connector is inserted through opening 833 and glued to the inside of support member 820, and electrically and physically attached to the contacts of second end 855 of heating element 850 such as by soldering.

Eye mask core assembly 800 uses standoffs 840 to dispose the front sides of eye-shaped portions 852 and 854 adjacent to the surface of the eyes, while suspending their back sides in free space. Moreover standoffs 840 are formed of a soft, flexible material such as foam to gently dispose heating element 850 adjacent to the eyes. By avoiding placing any significant pressure on the eyelids, eye mask core assembly 800 allows the user to wear the eye mask for extended periods of time without being uncomfortable or damaging the user's corneas. Moreover eye mask core assembly 800 does not use a cover, reducing product cost while giving the eye mask the appearance of goggles used in tanning booths.

Thus an eye mask has been described in various forms that ameliorates dry eye such as dry eye caused by meiobomian gland dysfunction, and dry eye that may be encountered in harsh environments such as low-humidity airplane cabins. In one form, the eye mask heats the eyelid to a lower temperature than known MGD treatments, such as 40° C., and thus is suitable for prolonged use. It operates using an eye mask core assembly surrounded by a covering such as a thin cotton cloth that spreads and holds the heat. The eye mask core assembly uses a heating element formed with a passive, serpentine conductor pattern formed on a flexible substrate. Since the heating element is formed with resistive elements, it can maintain an appropriate temperature without expensive thermal feedback and only requires the application of a relatively constant DC voltage obtainable from readily available power sources or generated from an AC mains power source using inexpensive components.

While various materials have been described for different components of the eye mask, it should be apparent that other suitable materials exist and may be used in place of those described above. For example, it is believed that covering 120 could be formed with a nylon covering of a suitable thickness instead of cotton. In the disclosed embodiments, the eye mask is held over the wearer's eyes using an elastic band surrounding the wearer's head. In other embodiments, the band can take other forms such as metal or plastic arms that fit over the wearer's ears like eyeglass arms. Moreover while different types of power supplies have been described, many other readily available power supplies may be used as well and at various voltages such as 5.5 volts, as long as the voltages and covering materials keep the eye temperature at a slightly elevated range.

Accordingly, it is intended by the appended claims to cover all modifications of the invention that fall within the true scope of the invention.

What is claimed is:

1. An eye mask, comprising:
   an eye mask core assembly having first and second eye-shaped portions separated by a distance corresponding to a separation of human eyes and having first and second ends, said eye mask core assembly producing heat in response to an application of a voltage thereto;
   a band attached to the first and second ends of said eye mask core assembly having first and second ends; and
   first and second insulated wires having first ends connected to said eye mask core assembly, and second ends for connection to a power supply,
   wherein said eye mask core assembly is constructed such that when the eye mask is attached to a user's head using said band, said eye mask core assembly disposes said first and second eye-shaped portions in direct contact with surfaces of, and without substantial pressure on, corresponding first and second eyelids of the user to conform to surfaces of corresponding eyeballs of the user,
   wherein said eye mask core assembly comprises:
      a support member attached to said first and second ends of said band; and
      a heating element attached to said support member and coupled to said first and second insulated wires and formed of a flexible substrate, said heating element comprising said first eye-shaped portion and said second eye-shaped portion which are separated by a center portion and a conductor, wherein said conductor in said center portion is configured to electrically connect said first and second eye-shaped portions but is not designed to produce heat, and has a serpentine pattern in said first and second eye-shaped portions producing heat in response to an application of power from said power supply.

2. The eye mask of claim 1, wherein when the eye mask is attached to the user's head using said band, said eye mask core assembly disposes first sides of said first and second eye-shaped portions in proximity to said human eyes and second sides of said first and second eye-shaped portions are in free space.

3. The eye mask of claim 1, wherein said eye mask core assembly further comprises:
   first and second standoffs each having a first end attached to said heating element and a second end attached to said support member such that said first end of said first standoff is attached to said heating element to the left of said first eye-shaped portion and said first end of said second standoff is attached to said heating element to the right of said first eye-shaped portion; and
   third and fourth standoffs each having a first end attached to said heating element and a second end attached to said support member such that said first end of said third standoff is attached to said heating element to the left of said second eye-shaped portion and said fourth standoff is attached to said heating element to the right of said second eye-shaped portion.

4. The eye mask of claim 3, wherein said first, second, third, and fourth standoffs are formed with a soft, flexible material.

5. The eye mask of claim 4, wherein said soft, flexible material comprises foam.

6. The eye mask of claim 1, wherein said heating element comprises a flexible polyimide film having a thickness of about 0.33 mm.

7. The eye mask of claim 1, wherein said conductor is formed with a nickel alloy film.

8. The eye mask of claim 1, wherein said support member is formed of a semi-rigid material.

9. The eye mask of claim 8, wherein said semi-rigid material comprises aluminum having a thickness between about 0.010 millimeters (mm) and 0.016 mm.

10. The eye mask of claim 1, wherein said band is formed of an elastic material.

11. The eye mask of claim 1, further comprising:
   a covering surrounding said eye mask core assembly.

12. The eye mask of claim 11, wherein said covering comprises a cloth made of cotton.

13. The eye mask of claim 1 further comprising:
   a connector coupled to said second ends of said first and second insulated wires and substantially compliant with the universal serial bus (USB) standard.

14. The eye mask of claim 1 further comprising:
   a connector coupled to said second ends of said first and second insulated wires and substantially compliant with the Feb. 5, 2009 version of the ANSI/SAE J563 standard.

15. An eye mask system, comprising:
   a regulated power supply for outputting a first voltage having approximately a predetermined value; and
   an eye mask core assembly coupled to said regulated power supply, comprising:
      a heating element coupled to and receiving power from said regulated power supply and formed of a flexible substrate, and having first and second heat producing areas which are separated by a center portion at a distance corresponding to a separation of human eyes and having first and second ends, said first and second heat producing areas producing heat in response to an application of power from said regulated power supply, and a conductor, wherein said conductor in said center portion is configured to electrically connect said first and second eye-shaped portions but is not designed to produce heat, and has a serpentine pattern in said first and second heat producing areas producing heat in response to an application of said first voltage; and
      an attachment system connected to said heating element for causing said heating element to conformally fit over human eyes, said attachment system constructed such that when the eye mask core assembly is attached to a user's head, said eye mask core assembly disposes said first and second heat producing areas in direct contact with surfaces of, and without substantial pressure on, corresponding first and second eyelids of the user to conform to surfaces of corresponding eyeballs of the user,
   wherein the eye mask system is characterized as being a feed-forward system without feedback.

16. The eye mask system of claim 15, wherein said predetermined value is from about 5.0 volts to about 6.0 volts.

17. The eye mask system of claim 15, wherein said regulated power supply comprises:
   a plug for connection to an alternating current (AC) mains outlet; and
   an AC-DC converter having an output coupled to said heating element.

18. The eye mask system of claim 15, wherein said first and second heat producing areas of said heating element are eye-shaped.

19. The eye mask system of claim 15, said first and second heat producing areas heat eyelids of said human eyes to approximately 40 degrees Celsius.

20. The eye mask system of claim 19, wherein said attachment system comprises:
   a support member having a first end and a second end;
   a band attached to the first end and to the second end of said support member; and
   first and second insulated wires having first ends connected to said heating element, and second ends for connection to said regulated power supply.

* * * * *